US009364431B2

(12) United States Patent
Callahan

(10) Patent No.: US 9,364,431 B2
(45) Date of Patent: Jun. 14, 2016

(54) INFUSED CARBOHYDRATE BASED GEL PAD FOR SUSTAINED ORAL TRANSMUCOSAL DELIVERY

(71) Applicant: Terence Vincent Callahan, Newport Beach, CA (US)

(72) Inventor: Terence Vincent Callahan, Newport Beach, CA (US)

( * ) Notice: Subject to any disclaimer, the term of this patent is extended or adjusted under 35 U.S.C. 154(b) by 175 days.

(21) Appl. No.: 13/937,336

(22) Filed: Jul. 9, 2013

(65) Prior Publication Data

US 2014/0017294 A1 Jan. 16, 2014

Related U.S. Application Data

(60) Provisional application No. 61/670,595, filed on Jul. 11, 2012.

(51) Int. Cl.

| | |
|---|---|
| ***A61K 9/00*** | (2006.01) |
| ***A61K 47/26*** | (2006.01) |
| ***A61K 31/133*** | (2006.01) |
| ***A61K 31/198*** | (2006.01) |
| ***A61K 31/465*** | (2006.01) |
| ***A61K 31/522*** | (2006.01) |
| ***A61K 31/7004*** | (2006.01) |
| ***A61K 47/36*** | (2006.01) |

(52) U.S. Cl.
CPC ............... *A61K 9/006* (2013.01); *A61K 31/133* (2013.01); *A61K 31/198* (2013.01); *A61K 31/465* (2013.01); *A61K 31/522* (2013.01); *A61K 31/7004* (2013.01); *A61K 47/26* (2013.01); *A61K 47/36* (2013.01)

(58) Field of Classification Search
CPC . A61K 31/133; A61K 31/198; A61K 31/465; A61K 31/522; A61K 31/7004; A61K 47/26; A61K 47/36; A61K 9/006
See application file for complete search history.

(56) References Cited

U.S. PATENT DOCUMENTS

| | | | | |
|---|---|---|---|---|
| 6,319,510 | B1 * | 11/2001 | Yates ............................ | 424/404 |
| 2004/0156794 | A1 * | 8/2004 | Barkalow et al. ............... | 424/48 |

* cited by examiner

*Primary Examiner* — Abigail Fisher
*Assistant Examiner* — Daniel L Branson
(74) *Attorney, Agent, or Firm* — The Dobrusin Law Firm, PC

(57) ABSTRACT

The present invention provides an infused carbohydrate based gel pad comprising: glucose polymer syrup, sugar, a hydrocolloid gelling agent, salt, acid, water and an infusing compound for oral transmucosal delivery wherein the gel pad (i) provides transmucosal delivery of active ingredients of the infusing compound into the bloodstream over a predetermined period of time; and (ii) possesses the property of adhesion to gum line tissue of an oral cavity and lack of adhesion to buccal tissue of the oral cavity. The present invention further provides a method of making the infused carbohydrate based gel.

18 Claims, No Drawings

INFUSED CARBOHYDRATE BASED GEL PAD FOR SUSTAINED ORAL TRANSMUCOSAL DELIVERY

CLAIM OF BENEFIT OF FILING DATE

This application claims the benefit of the filing date of U.S. Provisional Application Ser. No. 61/670,595 titled: "Infused Carbohydrate Based Gel Pad for Sustained Oral Transmucosal Delivery" filed on Jul. 11, 2012, which is incorporated herein by reference for all purposes.

FIELD OF INVENTION

The present invention relates to a carbohydrate based gel pad infused with an infusing compound that provides sustained oral transmucosal delivery of the infusing compound across the buccal areas of the mouth.

SUMMARY OF INVENTION

The present invention provides an infused carbohydrate based gel pad comprising; glucose polymer syrup, sugar, a hydrocolloid gelling agent, salt, acid, water and an infusing compound for compound for oral transbuccal, transdermal, and/or transmucosal (collectively hereinafter referred to as "transmucosal") delivery wherein the gel pad (i) provides transmucosal delivery of active ingredient(s) of the infusing compound into the bloodstream over a predetermined period of time: and (ii) possesses the property of adhesion to gum line tissue of an oral cavity for transmucosal delivery of the active ingredients) across buccal tissue of the oral cavity into the bloodstream.

The present invention provides a method of making an infused carbohydrate based gel comprising: (i) providing the ingredients of the gel pad comprising of the glucose polymer syrup, the sugar, the hydrocolloid gelling, the salt, the acid, the water and the infusing compound each at the desired concentration as measured by total weight of the formulation, (ii) mixing the glucose polymer syrup, the sugar, the hydrocolloid gelling agent, the salt, and the water together to form a composition and heating the composition to a first temperature for a first predetermined time period: (iii) adding and mixing the infusing compound and the acid into the composition and heating the composition at the second temperature for a second predetermined time period; (iv) pouring the composition into molds; and (v) heating the composition in the molds in an oven at a third temperature for a third predetermined time period until the composition within each mold reaches a predetermined water content and forms the gel pad: (vi) removing the gel pad from each of the molds.

DETAILED DESCRIPTION OF THE INVENTION

The passing of foods and other important metabolically important compounds through the stomach and liver is known as the first pass. This first pass greatly reduces the amount of micronutrients, ergogenic supplements, pharmaceuticals, and other metabolically active compounds ("infusing compounds") systematically available for absorption. Transmucosal delivery avoids the first pass stomach and liver degradation of such infusing compounds.

The present invention provides transmucosal delivery of the active ingredient(s) of one or more infusing compounds into the bloodstream over a predetermined period of time by using a carbohydrate based gel pad infused with the infusing compound(s). The transmucosal delivery system of the present invention avoids the first pass stomach and liver degradation of the infusing compound(s).

The present invention is an infused carbohydrate based gel pad comprising: glucose polymer syrup, sugar, a hydrocolloid gelling agent, salt, acid, water and an infusing compound for oral transmucosal delivery. The water acts as a solvent for dry ingredients and provides the gel pad with desired moisture. The gel pad may optionally include flavoring agent(s), coloring agent(s), preservatives, and stabilizers.

The glucose polymer syrup may be selected from any glucose polymer syrup suitable for oral consumption. Examples of glucose polymer syrup are sucrose syrup, brown rice syrup, white rice syrup, tapioca syrup, high fructose corn syrup, and a combination thereof. The glucose polymer syrup provides the gel pad with moisture, structure, sweetness, flavor, and caloric energy.

The sugar may be selected from any sugar suitable for oral consumption. Examples of sugar are glucose, dextrose, maltose, sucrose, ribose, fructose, mannitol, galactose, lactose, and a combination thereof. The sugar provides the gel pad with structure, sweetness, flavor and caloric energy.

The hydrocolloid gelling agent can be any hydrocolloid or gum that creates desirable gels and is suitable for use in products for oral consumption. Examples of the hydrocolloid gelling agent are pectin, agar, carrageenan, konjac/xanthan, locust bean gum/xanthan, gellan, alginate, and a combination thereof. The hydrocolloid agent provides gelation, thickening, gel-like structural support and stability to the gel pad.

The salt can be any suitable salt for oral consumption. Examples of the salt are sea salt, sodium chloride, sodium citrate, calcium citrate, potassium citrate, tri-potassium phosphate, and a combination thereof. The salt provides electrolytes, divalent cations, and flavor.

The acid can be any suitable acid for oral consumption. Examples of the acid are ascorbic acid, malic acid, citric acid, and a combination thereof. The acid may act as a pH regulator, stabilizer, preservative, and flavoring agent for the gel pad.

The infusing compound can be any suitable compound(s) desired for transmucosal absorption of its active ingredient (s). For example, the infusing compound may be a micronutrient, ergogenic supplement, a pharmaceutical composition, other metabolically active compound available and desired for transmucosal absorption or delivery. Examples of the infusing compound include but are not limited to caffeine, water soluble vitamins (e.g., B-complex and C, etc.), electrolytes (e.g., mineral salts, etc.), glutamine, choline, ribose, nicotine, nicotine substitutes, pharmaceuticals, and a combination thereof. The infusing compound should contain small molecules (e.g., molecules that are equal to or less than 500 atomic mass units) that can be absorbed via the transmucosal delivery route. The infusing compound may be water soluble or it can include carrier(s) that can transport non-water soluble substances chemically bonded to such carrier(s) across the derma barrier for transmucosal delivery. The active ingredient(s) contained within the infusing compound can be directly absorbed through the buccal tissues of the oral cavity into the bloodstream and delivered to cells throughout the body.

The gel pad is digestible and suitable for oral consumption. The gel pad functions as a sustained delivery system for transmucosal absorption of the active ingredient(s) of the infusing compound across the buccal areas of the oral cavity (e.g., mouth) over a predetermined period of time. The gel pad is generally placed along the gum (e.g., gingival) line. The gel pad exhibits the property of acting as a selective adhesive binding (e.g., sticking) to the gum line tissue, but not to the oral buccal areas of the mouth. This is due to the continual washing of the oral buccal tissue by saliva, which in turn dissolves the gel pad at the contact area of the buccal tissue, preventing adhesion and allowing for absorption of the active ingredient(s) of the infusing compound. In exemplary embodiments, the gel pad adheres to the gum tissue below the teeth, in the case of lower mouth application, or the gum tissue above the teeth, in the case of upper mouth application in seconds (e.g., approximately 30 seconds or the like). Furthermore, the gel pad can be placed along the gum line in the frontal area of the mouth behind the lips or next to one of the cheeks. Placement along the gum line next to one of the cheek may be more comfortable. The gel pad does come into sustained contact with (but does not adhere to) the oral buccal tissue allowing transmucosal absorption of the active ingredient(s) of the infusing compound into the bloodstream over a predetermined period of time.

Depending on the desired application, the gel pad is made in a variety of sizes, shapes (circular, oval, rectangular or square with smooth corners, bone shape, and other irregular shapes), thicknesses, and solid contents, which produce variations in time of melt (i.e., the amount of time of sustained contact with the oral buccal tissue) as well as surface area of contact with the oral buccal tissue. Consideration of comfort is a limiting factor in the size and shape of the gel pad and related total release time. Water moisture content is the defining limiting factor to the production of the desired characteristics of gel pad and total release time. Too high a water content would make the gel pad unstable and melt at low temperature. Extremely low water content produces a hard candy-like structure which is not the intent of the present invention and is undesirable due to the lack of adhesion property and comfort. In one exemplary embodiment, the gel pad is a semi-soft adhesive gel pad having a generally bone shape and weighs in the range between 0.5 gram to 5.0 gram having general dimensions of one inch in length, 0.5" inch in width, and 0.25" in height.

The composition of the gel pad can be modified to dissolve at different rates to allow variable time and sustained release of the infusing compound. Moreover, the gel pad may optionally provide two or more of the infusing compounds. Additionally, the gel pad can be layered during manufacture to allow for the stepped or differential delivery of two or more of the infusing compounds.

The present invention includes a method of making the gel pad discussed above. During manufacture, the gel pad is infused with the infusing compound(s). The invention is manufactured in steps by high heat application to boil liquid and dissolve any dry ingredients, evaporation to remove moisture following good manufacturing processes known to those in the confectionery or pharmaceutical industry. The gel pad is produced by combination and blending of its components described above. In one exemplary embodiment, the method of the present invention includes the following steps:

1. Provide the ingredients of the gel pad comprising of the glucose polymer syrup, the sugar, the hydrocolloid gelling agent, the salt, the acid, the water and the infusing compound in the following concentrations as measured by total weight of the manufacturing formulation ("formulation"): the glucose polymer syrup at a concentration ranging from about 40% to about 60%, from about 40% to about 55%, from about 40% to about 50%, and from about 40% to about 45%; the sugar at a concentration ranging from about 25% to about 45%, from about 25% to about 40%, from about 30% to about 40%, and from about 30% to about 35%; the hydrocolloid agent at a concentration ranging from about 1% to about 4%, from about 1% to about 3%, from about 2% to about 4%, from about 2% to about 3%; the salt at a concentration ranging from about 1% to about 7%, from about 2.5% to about 4%, from about 3% to about 6%, and from about 3% to about 4%; the acid at a concentration ranging from about 0.5% to about 3.0%, from 1% to about 2%, and from about 0.8% to about 1.2%; the water at a concentration ranging from about 8% to about 25%, from about 10% to about 20%, from about 10% to about 15%. The concentration of the infusing compound may vary depending upon the desired amount. Furthermore, the present invention includes embodiments wherein two or more infusing compounds are infused into the gel pad. Optional ingredients may include additional flavoring agent(s), coloring agent(s), preservatives, and/or stabilizers. The formulation discussed here may vary due to the desired composition and time release. All of the ingredients are weighed to desired percentage (e.g., concentration) of the formulation.

2. Mix the sugar, the hydrocolloid gelling agent, the salt, the water and the glucose polymer syrup together to form a composition and heat to a first temperature range that is from about 220 degrees Fahrenheit to about 300 degrees Fahrenheit, from about 225 degrees Fahrenheit to about 300 degrees Fahrenheit, or from about 220 degrees Fahrenheit to about 245 degrees Fahrenheit, while mixing (preferred constantly) for a first predetermined time period (e.g., about 7 to about 14 minutes) in order to mix in the ingredients thoroughly, to fully dissolve any dry ingredients, to reduce water content of the composition, and to break down the hydrocolloid agent.

3. Add and mix the infusing compound(s), the acid, and any optional ingredients into the composition and heat the composition for a second predetermined time period (e.g., about 30 seconds to about 5 minutes) at the second temperature range that is from about 180 degrees Fahrenheit to about 300 degrees Fahrenheit, from about 180 degrees Fahrenheit to about 245 degrees Fahrenheit, from about 195 degrees Fahrenheit to about 225 degrees Fahrenheit, or from about 200 degrees Fahrenheit to about 220 degrees Fahrenheit, until the composition reaches a desired water content percentage and dissolution of all ingredients into the composition while reducing any potential heat degradation of any heat sensitive ingredients especially the infusing compound(s), the acid, and/or any optional ingredients.

4. Pour the composition into molds (e.g., corn starch molds or the like) of desired shape and size.

5. Heat the composition in the molds in an oven at a third temperature range that is lower than the second temperature range (e.g., about 140 degrees Fahrenheit, from about 120 degrees Fahrenheit to about 160 degrees Fahrenheit, or the like) for a third predetermined time period (e.g., about 14 to about 36 hours) until the composition within each mold reaches a predetermined water content and forms the gel pad of the present invention. This process is known as curing. The specific temperature range varies with the third predetermined time period.

6. Cool the gel pad and remove the gel pad from each of the molds for packaging.

All ingredients listed above should be mixed thoroughly into the composition and if any of them are in solid forms, it is preferred that they are completely dissolved into the composition. Furthermore, the solid form ingredients may be optionally be first mixed and formed into a liquid solution by dissolving in water prior to being added to other ingredients and/or into the composition. For example, it is optional that the hydrocolloid gelling agent and the sugar are hydrated and mixed first with water without any heating. Moreover, it is also optional to mix during step 2 described above that the hydrated hydrocolloid gelling agent and sugar solution with the glucose polymer syrup first and heat to the first temperature range for a portion of the first predetermined time period before adding the salt and heat at the same temperature range for the remaining portion of the first predetermined time period. Similarly, it is optional to add the infusing compounds first to the composition and heat to the second temperature range for a portion of the second predetermined time period before adding the acid and other optional ingredients such as the flavoring agent, the coloring agent, preservatives, and/or stabilizers for the remaining portion of the second predetermined time period. It is also possible and optional that during step 3 described above that the infusing compounds are heated to the second temperature range at a portion of the second predetermined time period, and then the acid and other optional ingredients such as the flavoring agent, the coloring agent, preservatives, and/or stabilizers are added to the composition and heated to a temperature that is within the second temperature range but lower than the initial temperature(s) of the second temperature range (e.g., about 10 to 20 degrees Fahrenheit lower) for the remaining portion of the second predetermined time period (e.g., about 20 seconds to about 3 minutes). It is preferred but not required that the acid, if in dry form, is first hydrated with water before it is added into the composition.

The amount of the water used as a solvent for dissolution and hydration of the solid form ingredients is included in the amount of the water used for the formulation. During the steps 2 to 4, it is preferred that the composition is being constantly stirred. The present invention also contemplates the option of adding some of the ingredients first before adding the other ingredients within the same step. For example, the acid may be optionally added to the composition first while the composition is being heated at a specified temperature range before the addition of the infusing compound. The method of the present invention further includes the optional step of coating the gel pad with an art-disclosed edible finish that may also serve as protection from spoilage. Once the gel pads are manufactured, they can be packaged for consumption.

In another exemplary embodiment of the present invention, the method further includes providing a second composition by repeating the steps 1-3 discussed above except that the infusing compound(s) are different from the original composition. During the step 4 discussed above, the original composition is poured into the molds and then the second composition is poured on top of the original composition before resuming to the step 5 above. Furthermore, additional compositions can be manufactured by repeating the steps 1-3 discussed above wherein the infusing compound(s) for each of these compositions may be different. Each of these compositions is also poured into the mold in a similar fashion as described for the second composition before resuming to the step 5 above.

In yet another exemplary embodiment, the hydrocolloid gelling agent and sugar are first hydrated with water and mix for 5 minutes without heat. Other dry ingredients can also be hydrated with water at this time if desired. The next step is to mix the hydrated hydrocolloid gelling agent and sugar with the glucose polymer syrup to form a composition and heat the composition for 5 minutes at a temperature that is from about 220 degrees Fahrenheit to about 230 degrees Fahrenheit. This temperature is within the first temperature range. The next step is to add the salt directly into the heated composition for mixing and complete dissolution while heating for another 5 minutes at a temperature that is from about 230 degree Fahrenheit to about 240 degree Fahrenheit. This temperature is also within the first temperature range). The next step is to add the infusing compounds while the composition is still being heated at a temperature that is from about 200 Fahrenheit to about 220 Fahrenheit for 3 minutes. This temperature is within the second temperature range. The next step is to add the acids and any optional ingredients such as the flavoring agent, the coloring agent, preservatives, and/or stabilizers; and mix thoroughly for 2 minutes while allowing the temperature to fall slightly to a temperature that is from about 210 Fahrenheit to about 220 Fahrenheit. This temperature is also within the second temperature range. It is preferred but not required that the acid, if in dry form, is first hydrated with water before it is added into the composition. The next step is to pour the composition into the molds and heating in an oven at a temperature range of about 140 degrees Fahrenheit for 21 hours. The molds are removed from the oven and the gel pads in the molds are cooled (e.g., for approximately 24 hours) before removal from the molds (e.g., tumbling off the cornstarch). The gel pads are then optionally polished before they are sealed and packaged. The gel pad of the present invention delivers the active ingredient(s) of the infusing compound into the bloodstream via trans-mucosal oral absorption. The gel pad has many potential applications, including but not limited to, the sports nutrition industry, the pharmaceuticals industry, the tobacco industry, as well as any industry utilizing transmucosal or transdermal delivery via the oral buccal tissue. It is understood that the present invention as described and claimed herein can be used for many additional purposes, therefore the invention is within the scope of other fields and uses and not so limited.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes.

The following example provided in accordance to the present invention is for illustrative purpose only and is not intended as being exhaustive or limiting of the invention.

EXAMPLE I

Gel pad is made from the formulation comprising: brown rice syrup at a concentration of 40.5% (the glucose polymer syrup); cane sugar at a concentration of 30.5% (the sugar); pectin and agar at a combined concentration of 2.6% (the hydrocolloid gelling agent); water at a concentration of 13% sea salt and sodium citrate at a combined concentration of 3.2% (the salt); abscorbic acid and malic acid at a combined concentration of 0.8% (the acid); glutamine, B vitamins (e.g., B-3, B-4, B-6, B-12), choline, ribose, caffeine and potassium phosphate at a combined concentration of 9.5% (the infusing compounds); and optional ingredients such as the flavoring agent and the coloring agent. The concentration percentages stated in this Example are all based upon total weight of the formulation. The ingredients are used to produce gel pads in an open kettle system. Other art-disclosed systems may be used to produce the gel pads of the present invention and these systems may change the temperatures used in the heating and curing process. One skilled in the art can determine the proper and desired temperatures required for these systems.

The first step is to hydrate the hydrocolloid gelling agent (pectin and agar) and cane sugar with water and mix for 5 minutes without heat Other dry ingredients can also be hydrated with water at this time if desired. The next step is to mix the hydrated hydrocolloid gelling agent and cane sugar with the glucose polymer syrup (brown rice syrup) to form a composition and heat the composition for 5 minutes at a temperature that is from about 220 degrees Fahrenheit to about 230 degrees Fahrenheit. This temperature is within the first temperature range. The next step is to add the salt (sea salt and sodium citrate) directly into the heated composition for mixing and complete dissolution while heating for another 5 minutes at a temperature ranging from about 230 Fahrenheit to about 240 Fahrenheit. This temperature is also within the first temperature range. The next step is to add the infusing compounds while the composition is still being heated at a temperature that is from about 200 Fahrenheit to about 220 Fahrenheit for 3 minutes. This temperature is within the second temperature range. The next step is to add the acids and any optional ingredients such as the flavoring agent, the coloring agent, preservatives, and/or stabilizers; and mix thoroughly for 2 minutes while allowing the temperature to fall slightly to a temperature that is from about 210 Fahrenheit to about 220 Fahrenheit. This temperature is still within the second temperature range. It is preferred but not required that the acids are first hydrated with water before they are added into the composition. The next step is to pour the composition into the molds and heating in an oven at a temperature of about 140 degrees Fahrenheit for 21 hours. The molds are removed from the oven and the gel pads in the molds are cooled (e.g., for approximately 24 hours) before removal from the molds (e.g., tumbling off the cornstarch). The gel pads are then optionally polished before they are sealed and packaged.

What is claimed is:

1. An infused carbohydrate based gel pad comprising: glucose polymer syrup, sugar, a hydrocolloid gelling agent, salt, acid, water and an infusing compound for oral transmucosal delivery wherein the gel pad (i) provides transmucosal delivery of active ingredients of the infusing compound into the bloodstream over a predetermined period of time; and (ii) possesses the property of adhesion to gum line tissue of an oral cavity for transmucosal delivery of the active ingredients across buccal tissue of the oral cavity into the bloodstream wherein the gel pad is made from the following formulation of ingredients: the glucose polymer syrup at a concentration ranging from about 40% to about 60%; the sugar at a concentration ranging from about 25% to about 45%; the hydrocolloid agent at a concentration ranging from about 1% to about 4%; the salt at a concentration ranging from about 1% to about 7%; the acid at a concentration ranging from about 0.5% to about 3.0%; the water at a concentration ranging from about 8% to about 25% wherein concentrations of the ingredients are all measured based upon total weight of the formulation.

2. The gel pad of claim 1 wherein the glucose polymer syrup is selected from the group consisting of sucrose syrup, brown rice syrup, white rice syrup, tapioca syrup, high fructose corn syrup, and a combination thereof.

3. The gel pad of claim 1 wherein the sugar is selected from the group consisting of glucose, dextrose, maltose, sucrose, ribose, fructose, mannitol, galactose, lactose, and a combination thereof.

4. The gel pad of claim 1 wherein the hydrocolloid gelling agent is selected from the group consisting of pectin, agar, carrageenan, konjac/xanthan, locust bean gum/xanthan, gellan, alginate, and a combination thereof.

5. The gel pad of claim 1 wherein the salt is selected from the group consisting of sea salt, sodium chloride, sodium citrate, calcium citrate, potassium citrate, tri-potassium phosphate, and a combination thereof.

6. The gel pad of claim 1 wherein the acid is selected from the group consisting of ascorbic acid, malic acid, citric acid, and a combination thereof.

7. The gel pad of claim 1 wherein the infusing compound is selected from a group consisting of micronutrients, ergogenic supplements, pharmaceutical compositions, caffeine, water soluble vitamins, electrolytes, glutamine, choline, ribose, nicotine, nicotine substitutes, pharmaceuticals and a combination thereof.

8. The gel pad of claim 1 further comprising a compound selected from the group consisting of flavoring agents, coloring agents, preservatives, stabilizers, and a combination thereof.

9. The gel pad of claim 1 wherein the gel pad is separated into layers and each layer contains at least one different type of the infusing compound compared to the other layers.

10. A method of making the infused carbohydrate based gel of claim 2 comprising:

(i) providing ingredients of the gel pad formulation comprising: glucose polymer syrup, sugar, a hydrocolloid gelling agent, salt, acid, water and an infusing compound each at a desired concentration as measured by total weight of the formulation;

(ii) mixing the glucose polymer syrup, the sugar, the hydrocolloid gelling agent, the salt and the water together to form a first composition and heating the first composition to a first temperature range for a first predetermined time period;

(iii) adding and mixing the infusing compound and the acid into the first composition and heating the first composition at a second temperature range for a second predetermined time period;

(iv) pouring the first composition into molds; and (v) heating the first composition in the molds in an oven at a third temperature range for a third predetermined time period until the first composition within each mold reaches a predetermined water content and forms the gel pad; and (vi) removing the gel pad from each of the molds.

11. The method of claim 10 wherein the glucose polymer syrup is selected from the group consisting of sucrose syrup, brown rice syrup, white rice syrup, tapioca syrup, high fructose corn syrup, and a combination thereof.

12. The method of claim 10 wherein the sugar is selected from the group consisting of glucose, dextrose, maltose, sucrose, ribose, fructose, mannitol, galactose, lactose, and a combination thereof.

13. The method of claim 10 wherein the hydrocolloid gelling agent is selected from the group consisting of pectin, agar, carrageenan, konjac/xanthan, locust bean gum/xanthan, gellan, alginate, and a combination thereof.

14. The method of claim 10 wherein the salt is selected from the group consisting of sea salt, sodium chloride, sodium citrate, calcium citrate, potassium citrate, tri-potassium phosphate, and a combination thereof.

15. The method of claim 10 wherein the acid is selected from the group consisting of ascorbic acid, malic acid, citric acid, and a combination thereof.

16. The method of claim 10 wherein the infusing compound is selected from a group consisting of micronutrients, ergogenic supplements, pharmaceutical compositions, caffeine, water soluble vitamins, electrolytes, glutamine, choline, ribose, nicotine, nicotine substitutes, pharmaceuticals and a combination thereof.

17. The method of claim 10 wherein during the step (iii), at least one of the compounds selected from the group consisting of flavoring agents, coloring agents, preservatives, stabilizers, and a combination thereof, is added to the first composition.

18. The method of claim 10 wherein the method further comprising of (a) making a second composition by repeating the steps (i) to (iii); (b) pouring the second composition into the molds in the step (iv) after the first composition has been poured into the molds in the step (iv).

* * * * *